United States Patent [19]
Edelman et al.

[11] Patent Number: 5,540,928
[45] Date of Patent: * Jul. 30, 1996

[54] EXTRALUMINAL REGULATION OF THE GROWTH AND REPAIR OF TUBULAR STRUCTURES IN VIVO

[75] Inventors: Elazer R. Edelman, Brookline; David H. Adams, Boston; Morris J. Karnovsky, Newton Centre, all of Mass.

[73] Assignee: President and Fellows of Harvard College, Cambridge, Mass.

[ * ] Notice: The term of this patent shall not extend beyond the expiration date of Pat. No. 5,527,532.

[21] Appl. No.: 234,714

[22] Filed: Apr. 28, 1994

Related U.S. Application Data

[63] Continuation of Ser. No. 656,182, filed as PCT/US90/06628 Nov. 13, 1990, abandoned.

[51] Int. Cl.$^6$ ............................. A61F 2/00; A61K 9/22
[52] U.S. Cl. .................... 424/422; 424/423; 424/424; 424/425; 514/56
[58] Field of Search ...................... 424/422, 423, 424/424, 425; 514/56, 423, 12

[56] References Cited

U.S. PATENT DOCUMENTS

| | | | |
|---|---|---|---|
| 3,797,485 | 3/1974 | Urquhart | 424/422 |
| 3,993,071 | 11/1976 | Higuchi et al. | 128/260 |
| 4,391,797 | 7/1983 | Folkman et al. | 424/19 |
| 4,495,174 | 1/1985 | Allock et al. | 424/78 |
| 4,808,402 | 2/1989 | Leibovich | 424/423 |
| 4,898,732 | 2/1990 | Fernandez | 424/422 |
| 5,120,322 | 6/1992 | Davis | 604/265 |

OTHER PUBLICATIONS

O'Reilly in The Pharmacologic Basics of Therapeutics, 7th ed. Gilman et al ed McMillian Pub. Co. 1985, p. 1338.
Powell et al Science 245, 186 (1989).
Castellot et al J. Cell Physiol. 120, 315 (1984).
Molino et al Min. Cardioang. 21, 553 (1973).
Okada et al Neurosurg. 25, 892, 1989.
Okada et al. Stroke 19, 1470, 1988.
Mayberg et al., 1988, Surgical Forum 39:496–499.
Okada et al., 1988, Stroke 19:1470–1476.
Okada et al., 1989, Neurosurgery 25:892–898.
Cotran et al., 1989, Robbins Pathologic Basis of Disease, pp. 73–74, pp. 253–254, pp. 553–557 and pp. 562–565.
Mayberg et al., 1981, Science 213:228–230.
Moskowitz et al., 1981, Brain Research 212:460–465.
McBride et al., The New England Journal of Medicine, vol. 318, No. 26, 1734–1734 (1988).
Simpfendorfer, Cleveland Clinic Journal of Medicine, vol. 55, No. 5, 429–432 (1988).
Fishman et al., Laboratory Investigation, vol. 32, No. 3, 339–351 (1975).
Austin et al., J. Am. Coll. Cardiol., vol. 6, No. 2, 369–375 (1985).
Diaz–Flores et al., Virchows Arch (Pathol Anat), Vo. 406:165–177 (1985).
Steele et al., Circulation Research, vol. 57, No. 1, 105–112 (1985).
Clowes et al., Nature 265:625–626 (1977).
Castellot Jr., et al., J. Cell. Phys. 120:315–320 (1984).
Castellot Jr., et al., J. Cell Biology 102:1979–1984 (1986).
Jaques, Artery, vol. 14, No. 4, 209–215 (1987).
Bick et al., Seminars in Thrombosis and Hemostasis, vol. 11, No. 2, 213 –217 (1985).
Mahadoo et al., Medical Hypotheses 5:825–841 (1979).

(List continued on next page.)

*Primary Examiner*—Gollamudi S. Kishore
*Attorney, Agent, or Firm*—Fish & Richardson, P.C.

[57] ABSTRACT

A method of regulating repair in a physiological system following injury to the lumen of a tubular structure in that system, and of testing the effectiveness of regulatory agent, is presented. The method includes administering a modulator of cell or tissue growth to an extraluminal site adjacent the injured tissue.

5 Claims, 1 Drawing Sheet

OTHER PUBLICATIONS

Mahadoo et al., Artery, vol. 7, No. 5, 438–477 (1980).
Larsen et al., Proc. Natl. Acad. Sci. USA, 83:2964–2968 (1986).
Bentley et al., Thrombosis Research 18:177–187 (1980).
Dawes et al., Thrombosis Research 44:683–693 (1986).
Habib et al., Circulation Research vol. 58, No. 2, 305–309 (1986).
Whitworth et al., J. Am. Coll. Cardiol., 8:1271–1276 (1986).
Powell et al., Science 245:186–188 (1989).
Gordon et al., Circ. Supp. Abstracts of the 60th Scientific Sessions, vol. 76, No. 4, IV–213 (1987).
Langer et al., Methods in Enzymology, 112:399–423 (1985).
Brown et al., J. Pharm. Sci., vol. 72, No. 10, 1181–1185 (1983).
Sparer et al., J. Controlled Release 1:23–32 (1984).
Lawter et al., Proceed. Intern. Symp. Control Rel. Bioact. Mater, 14: 99–100 (1987).
Neenan et al., Biomaterials, 3:78–80 (1982).
Grolleman et al., J. Controlled Release, 3:143–154 (1986).
Ellis et al., Circ. Supp. Abstracts of the 60th Scientific Sessions, vol. 76, No. 4, IV–213 (1987).
Langer et al., Annals New York Academy of Sciences, 446:1–13 (1985).
Stemerman et al., J. Exp. Med. 136:769–789 (1972).
Guyton et al., American J. Path. 94:585–596 (1979).
Castellot Jr., et al., J. Cell Biol. 90:372–379 (1981).
Molino et al., Min. Cardioang. 21:553–557 (1973).
O'Reilly, The Pharmacologic Basics of Therapeutics, 7th ed., Gilman et al., eds., Macmillan Publishing Co. (1985).
Mahadoo, International Symposium on Heparin, Saskatoon, Sask., (1977).
Jaques et al., Seminars in Thrombosis and Hemotasis 4:298–325 (1978).
Kakkar, Thrombos. Diathes. Haemorrh., 33:87–96 (1974).
Gallus, Seminars in Thrombosis and Hemostatis, 2:232–290 (1976).

EXTRALUMINAL REGULATION OF THE GROWTH AND REPAIR OF TUBULAR STRUCTURES IN VIVO

This is a continuation of application Ser. No. 07/656,182, filed as PCT/US90/06628, Nov. 13, 1990, now abandoned.

BACKGROUND OF THE INVENTION

This invention relates to the general field of regulation of the growth and repair of tubular, or luminal, structures.

Tubular structures within the body (including bronchi of the lung, the entire gastrointestinal tract from the esophagus to the anus, the ureters and urethra of the genitourinary system, the fallopian tubes and vas deferens of the reproductive system, and the blood vessels) are all subject to luminal constriction and obstruction to flow. As a result, tissues and organs downstream of the obstruction are deprived of vital elements and tissues and organs upstream are dammed up with fluid and/or toxic products.

Surgical repair is often indicated in an attempt to relieve these obstructions. However, the repair may be unsuccessful or short-lived due to accelerated obstruction and a recurrence of the events that led to the initial crisis. Overproliferation of smooth muscle cells (SMC) as part of the natural repair process may contribute to luminal occlusion. In the arterial system, for example, restenosis rates of 25 to 35% have been noted within three months following percutaneous balloon angioplasty, and current estimates of the life expectancy of saphenous venin bypass grafts do not exceed 7 years. In the gastrointestinal system, this same phenomenon presents as recurrent bowel obstruction after lysis of adhesions or surgical anastomotic repair, and in the reproductive system as an ineffective surgical repair of the fallopian tubes or vas deferens.

There have been various attempts to limit occlusion. For example, for blood vessels, effort has been directed at various circulating (intravenous) factors such as heparin. Such factors inhibit or stimulate the clotting process and may also affect smooth muscle cell proliferation. Attempt have also been made to control environmental factors such as blood pressure, cholesterol, or smoking (nicotine). As regards lungs, attempts to limit occlusion have been directed at aerosolized factors and modulators of vascular tone (e.g., bronchodialators) and control of mucous formation. Efforts concerning the genitourinary system have focused on maintaining adequate flow, e.g. by controlling pH to enhance the solubility of stone material or by mechanical means such as ultrasound energy to break-up stones or uretal stents.

SUMMARY OF THE INVENTION

In general, one aspect of the invention features a method of regulating repair following injury to luminal tissue that includes administering a modulator of cell or tissue growth at an extraluminal site adjacent the injured tissue. "Regulating repair" is meant to include controlling luminal occlusion (e.g., the reduction or the prevention of formation of such occlusion). By luminal tissue is meant the tissue, primarily endothelium, in the lumen of a tubular structure. A modulator is an agent that effects a change in the rate of cell or tissue growth. An extraluminal site is one located outside and adjacent to the injured tubular structure, one example being the adventitia, the layer of loose connective tissue forming the outermost coating of an organ.

Preferred embodiments of the invention include the following features. The invention is particularly appropriate for controlling repair of the vascular system, preferably repair of an artery, and the preferred modulating agent is either anticoagulant or non-anticoagulant heparin. The modulator preferably is delivered to the adventitia adjacent the artery in a polymer matrix (e.g., an ethylene-vinyl acetate copolymer), at a rate of from 1 µg to 100 mg/day, for a period of at least 24 hours. Other sites of injury for which the method is particularly appropriate include the fallopian tubes or the vas deferens of the reproductive system, the ureter or the prostate gland of the genitourinary system, the bowel of the gastrointestinal system, or the trachia or the bronchial tree of the pulmonary system. Other vehicles for administration include aqueous gels, foams, or sprays (e.g. aerosolized).

In another aspect, the invention generally features a method of testing the effectiveness of a modulator in regulating repair following injury to luminal tissue that includes administering the modulator to an extraluminal site adjacent the tissue and determining the extent of regulation of repair following such administration.

Local administration of a modulating agent to an extraluminal site adjacent an injured luminal structure or organ allows for orderly repair of the injured endothelium while reducing detrimental side effects of other forms of administration.

Another aspect of the invention features a controlled release polymer device that includes a capillary action release optimizing element that may also serve to immobilize the device at a local site, e.g. to the outside of a lumen. The device comprises a controlled release polymer matrix (such as one described above) loaded with a drug, e.g., a cell-growth modulating agent according to the invention. The device is configured as a solid encasing a portion of the release optimizing element, which is configured as an elongated fibrous suture and preferrably is made from a material that supports capillary action and is suitable for immobilizing the polymer body. The release optimizing element may take the form of a suture (made from standard suturing materials) which itself is not impregnated with drug. Preferably, the outer solid surfaces are coated to retard release of the modulator from coated surfaces. Also preferably, the polymer is shaped as a torroidal structure or a disc with a generally central opening (preferably the opening is a hole extending completely through the polymer body) containing the release element. This aspect of the invention is particularly adapted to matricies that provide diffusion controlled release. This aspect of the invention provides various advantages. The element is firmly anchored. The wicking effect of the element increases efficiency by reducing the total amount of drug residing in the matrix when release effectively ends. The kinetics of release (rate of release over time) is more stable.

Other features and advantages of the invention will be apparent from the following description of the preferred embodiment thereof, and from the claims.

DESCRIPTION OF THE PREFERRED EMBODIMENT

Figure 1A:
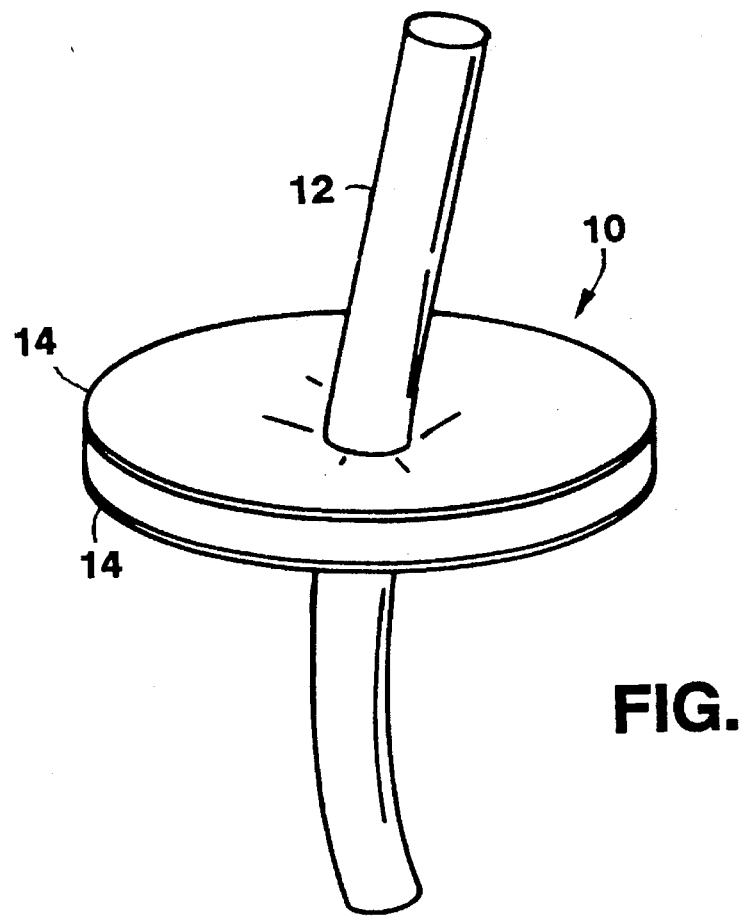

The method of the invention permits local administration of a modulator of cell or tissue growth to the outside of a tubular (or luminal) physiological structure for the purpose of regulating the repair of that structure following injury, for example, by surgical procedures. Examples of systems containing such structures and typical surgical procedures where regulating the repair process would be valuable are the vascular system (e.g., vascular anastomses that accompany procedures such as organ transplant, coronary by-pass surgery, systemic arterio-arterio and arterio-venus bypass surgery, and arterio-venus shunts that accompany vascular access for dialysis); the reproductive system (reversal of tubal ligation or vasectomy); genitourinary system (prostate surgery); gastrointestinal system (anastomotic repair of a bowel obstruction); and the pulmonary system (repair or reconstruction of traumatic or surgical injury to trachial or bronchial structures).

A wide range of growth modulating agents are appropriate for use in carrying out the method of the invention including those indicated as affecting angiogenesis, smooth muscle cell proliferation or vascularization. Some examples (as described in more detail below) include: heparin; the angiotensin converting enzyme inhibitors (e.g., captopril); angiotensin; angiogenic growth factors; heparin binding growth factors (See U.S. Pat. No. 4,882,275), particularly fibroblast growth factor; platelet derived growth factor (PDGF); transforming growth factor-β (TGF-β); immunosupressants (e.g., cyclosporine); calcium channel inhibitors (e.g., nifedipine); as well as cytokines and interleukins which control cell-cell interaction during vascular or other luminal tissue repair in response to injury.

The modulator may be delivered to the appropriate site outside the tubular structure of interest in a delivery system, e.g., a matrix composed of the modulator in solid form and a polymer, such as an ethylene-vinyl acetate copolymer (described in detail below). The polymer matrix delivery system can be made from any generally inert biocompatible polymer material. The material can be formed in a matrix as described below, or it can be in capsule form or other known controlled release configurations. Desired kinetics for the release of a particular drug can be achieved by known techniques by controlling the matrix fabrication techniques or the nature of the polymer of the delivery system.

A polymer matrix system to deliver the modulating agent is particularly useful when the substance to be delivered is unstable in solution, rapidly degraded, prone to precipitation, or of limited solubility. Alternate delivery systems which may be especially appropriate for modulating agents include bioerodible systems such as polyorthoester systems described in Sparer et al., *J. Controlled Release* 1:23–32 (1984); poly (glycolide-CO-DL-lactide) microcapsules disclosed in Lawter et al., *Proc. Int'l. Symp. Control. Rel. Bioact. Mater.* 14:99–100 (1987); and poly (organophosphazene) bound drugs as disclosed by Neenan and Allcock, *Biomaterials* 3: 78–80 (1982), and Grolleman et al., *J. of Controlled Release* 3: 143–154 (1986).

A particularly preferred polymer release matrix is the ethylene-vinyl acetate copolymer (EVAc) matrix described in Folkman and Langer U.S. Pat. No. 4,391,797, hereby incorporated by reference.

A particularly preferred cell and tissue growth modulating agent is heparin, an α,β-glucosidically linked, highly sulfated copolymer of uronic acid and glucosamine. Preparations are polydisperse with a molecular weight range of from 5,000–40,000 daltons. The precise composition of commercial heparin and the precise degree of antiproliferative activity vary depending on the source and method of purification. By the term "heparin," we mean to include all forms of heparin and all fragments of heparin having an antiproliferative effect, e.g., both anticoagulant heparin and non-anticoagulant heparin (e.g., heparin that is identified by its failure to bind to an anti-thrombin III affinity column) have antiproliferative activity. Other well known methods of preparing non-anticoagulent heparin include modification of native heparin by periodate oxidation or by enzymatic degradation, and de novo synthesis.

To establish loading of a matrix, drug release in vivo from the matrix (e.g. an EVAc matrix) is assumed to mirror release in vitro (Brown et al., *J. Pharm. Sci.* 72:1181–1185 (1983)). The maximum number of units of modulator to be applied directly to the extraluminal tissue (e.g., an arterial wall) can be estimated by using in vitro release data. Animal models such as those described below provide a dose response curve. To scale up from animal to human delivery, e.g., in human arteries, one considers only the difference in luminal diameter (e.g., scaling up from rat to human vessel diameter involves a factor of approximately four to tenfold). Because achieving systemic effects is not desired, body weight does not enter into the calculation.

At the time of surgical intervention of a typical surgical procedure, the polymer matrix embedded with the modulator is placed at an extraluminal site (e.g., in the adventitia) adjacent the injured lumen (e.g., artery) and the adjacent muscles and facia are sutured closed to insure immobilization of the matrix. During recovery of the patient, fluid is absorbed by the matrix and solubilizes the modulator, which then diffuses in solution through the channels of the matrix and out into the adventitia. Positioning of the matrix in the adventitia assures that heparin delivery takes place at the exterior surface of the blood vessel wall, at the site of injury.

The following examples of specific procedures, modulators and delivery systems used in animal models are provided to illustrate and not to limit the invention.

EXAMPLE 1

Heparin, particularly non-anticoagulent heparin, can be administered to an artery from an EVAc slow release matrix according to the following example.

An EVAc matrix loaded with 0.1–1000 mg (most preferably 0.5–500 mg) non-anticoagulant heparin is prepared as described below. As part of the surgical procedure, (e.g. coronary by-pass or coronary valve replacement) the matrix is sutured in the adventitia adjacent the artery. The adjacent muscles and facia are sutured closed to immobilize the matrix adjacent the arterial repair. The heparin is released at a rate of 1 µg–100 mg/day, for more than one (preferably more than three, and most preferably more than seven) days.

EXAMPLE 2

Anti-coagulant (AC) heparin (Choay Heparin 1453, m.w. 12,000–18,000 dalton, U.S.P. 160 U/mg, in vitro antiproliferative activity 80% (as described by Castellot et al. (1987) *Seminars in Thrombosis and Hemostasis* 13:489–503) or non-anti-coagulant (NAC) heparin (Choay heparin 1772, m.w. 5000–8000 dalton, U.S.P. 10 U/mg, in vitro antiproliferative activity 80%), Choay Institute, Paris, France, were embedded in polymer matrices using a solvent casting technique as described in Langer et al., *Methods in Enzymol.* 112:399–423 (1985). First, ethylene-vinyl acetate copolymer (ELVAX-40P, 40% vinyl acetate, E. I. DuPont, Wilm., Del. or U.S.I. of Cincinnati, Ohio) was dissolved in methylene chloride to a concentration of 10% (w/v). Dry powdered heparin was then sieved to particle sizes less than 180 microns and added to the EVAc solution. If the heparin aggregated, the drug was dissolved in normal saline, lyophylized to a powder, pulverized with mortar and pestle in a humidity controlled box and then sieved and added to the dissolved EVAc. The drug-polymer suspension was vortexed, let stand for 15 seconds to allow air bubbles to settle out and then poured into glass molds that had been precooled on dry ice. At these temperatures, the heparin was immediately frozen in place so as to be uniformly distributed through the matrix and not settle on the bottom. The resultant matrix was a homogeneous dispersion of heparin within EVAc. Once hardened, the matrices were removed from their glass molds, placed in a −20° C. freezer for two days and then under vacuum (600 mtorr) for another two days.

For use, smaller pellets were cut from the larger slabs to specific sizes and weights, and a coating was applied by placing a 20 gauge intravenous needle one cm into the center of the face of the matrix pellet and then immersing the pellet in a solution of 10% EVAc dissolved in methylene chloride for 5 seconds. As the pellets were withdrawn from the solution, they were spun slowly for a minute to allow for uniform coating. This entire process was repeated twice more. The matrices were left on the needles and placed in a chemical fume hood to allow for further solvent evaporation. After 12 hours, the extraneous polymer material that had migrated up the needle was removed by spinning a tweezers around the base of the needle as it was withdrawn from the matrix pellets. This insured that the extra polymer material did not collapse over the hole and that the hole remained open. Matrices were stored in a dessicator where solvent evaporation continued to completion.

Male Sprague-Dawley rats (300–500 gm, Charles River Breeding Laboratories, Wilmington, Mass.) were anesthetized with sodium nembutol 0.5 mg/gm body weight, and supplemental anesthesia was maintained with ether inhalation. A midline incision was made from the mandible to the mid-sternum. The carotid artery was exposed along the length of the bifurcation with blunt dissection, and the external carotid artery was isolated and ligated in its cephalad portion. A 2 French Fogarty balloon catheter (American Edwards Laboratories, Santa Ana, Calif.) was introduced into the arteriotomy of the external carotid artery and passed in its inflated state over the endothelium of the common carotid artery three times. The catheter was then deflated and removed from the external carotid artery, which was then ligated. In different groups of animals, EVAc matrices containing no drug, AC heparin or NAC heparin were placed adjacent to the injured artery. The adjacent muscles and fascia were sutured closed with 4-0 nylon suture to insure immobilization of the pellet. The midline incision was closed with the same suture and animals observed in separate cages during recovery. As a control, to demonstrate that the effect at issue is specific for adventitial or extraluminal delivery, EVAc matricies were placed in a subcutaneous pocket over the animal's dorsal neck region. In other animals, an osmotic infusion pump (ALZA Corporation, Palo Alto, Calif.) provided continuous iv administration of these same agents. The pumpϕ5X was placed in a pocket made in the neck of the rat, and a silastic catheter extended from the pump to the right internal jugular vein. AC and NAC heparins were mixed in lactated Ringer's solution and delivered at 0.3 mg per kilogram of body weight per hour. Control animals received lactated Ringer's infusion. The overall doses of the drugs administered are displayed in Table I.

TABLE I

| | HEPARIN DOSAGE mg (over 14 days) | | |
|---|---|---|---|
| | | MATRICES | |
| | INTRAVENOUS | CAROTID | DORSAL |
| NAC | (5) 25.9–43.3* | (10) 19.5 ± 1.9 | (5) 18.5 ± 2.9 |
| AC | (5) 25.9–43.3* | (8) 8.1 ± 1.9 | (4) 7.1 ± 0.2 |

*set to 0.3 mg/kg/hr and dictated by the size of the animal numbers in parentheses represent the number of animals in each group As an indication of anti-coagulation activity, activated partial thromboplastin times (aPTT) were determined within the first 24–36 hours after the procedure and at day 14. To observe the percent of luminal occlusion, animals were euthanized while undergoing intravascular fixation perfusion using methods described in A. W. Clowes et al., *Lab, Invest.* 49:327 et seq. (1983). Photomicrographs of all arterial sections were obtained, and the percent of luminal occlusion was calculated for each arterial segment using computerized digital planimetry. Specifically, the natural lumen boundary is apparent by photomicroscopy. The boundary is extended inwardly by inclusions. Digital planimetry is used to provide a measure of the cross-sectional area of the natural lumen boundary, divided into the area of the inclusion, yielding percent occlusion.

Anti-coagulation activity as given by the aPTT (Table II) and extent of luminal occlusion (Table III), for each animal group, are detailed below.

TABLE II

| | aPTT (sec) | | |
|---|---|---|---|
| | | MATRICES | |
| | INTRAVENOUS | CAROTID | DORSAL |
| CONTROL | (6) 16.2 ± 0.1 | (8) 16.5 ± 0.4 | |
| NAC | (5) 18.4 ± 0.6 | (10) 15.0 ± 0.4 | (5) 17.5 ± 0.5 |
| AC | (5) 40.0 ± 11.8* | (8) 15.3 ± 0.1 | (4) 17.0 ± 1.0 | numbers in parentheses represent the number of animals in each group
statistical significance compared with corresponding controls: *p<0.0005

TABLE III

| | LUMINAL OCCLUSION (%) | | |
|---|---|---|---|
| | INTRA- | MATRICES | |
| | VENOUS | CAROTID | DORSAL |
| CONTROL | (6) 52.2 ± 4.2 | (8) 55.9 ± 4.3 | |
| NAC | (5) 46.4 ± 3.9 | (10) 17.7 ± 3.78@ | (5) 45.0 ± 2.0 |
| AC | (5) 16.8 ± 4.3** | (8) 9.4 ± 2.6* | (4) 28.0 ± 2.6 | numbers in parentheses represent the number of animals in each group
statistical significance compared with corresponding controls: *p<0.0005, **p<0.0003, @ p<0.0001

Referring to Table II, only the intravenous administration of AC heparin produced systemic anticoagulation. Neither the local matrix delivery of either heparin, in subcutaneous or adventitial positions, nor the intravenous infusion of NAC heparin had any discernable effect on clotting function. None of the animals in any groups suffered from excessive bleeding. Referring to Table III, intravenous AC heparin infusion reduced luminal occlusion 68%, from a control value of 52.2 to 16.8%. NAC heparin delivered in the same fashion achieved only an 11% reduction (no statistical difference in comparison to control). Subcutaneous matrix delivery of NAC heparin also showed no significant difference in luminal occlusion, but similar delivery of AC heparin reduced occlusion by 52%. The largest effect on luminal occlusion was observed with adventitial delivery. Occlusion was reduced from 55.9% to 9.4% (83% reduction) in animals with AC heparin matrices, and to 17.7% (68% reduction) in animals with NAC heparin matrices.

EXAMPLE 3

To generate a dose response curve for NAC heparin, twelve rats were implanted with NAC heparin-bearing matrices of different net weights so as to deliver different dosages of heparin over the 14 day period. As the dose of the NAC heparin was increased, the effect on SMC proliferation rose, such that at the highest dose tested, NAC heparin inhibited SMC proliferation to an equal extent as AC heparin, at five times the equivalent dose. A dose response experiment was not performed for AC heparin as the amount of heparin delivered in the uniform dose study was already low and had achieved over 80% inhibition of SMC proliferation.

At a rate of about 0.8 mg/day for in vitro release, the maximum amount of heparin human arteries would be exposed to would be no higher than 20–50 units/hour, and systemic levels would be undetectable. This is in marked contrast to the 1000–1500 units/hour of i.v. infusion currently used in clinical practice for systemic anticoagulation.

The local, extraluminal action of the least potent of this class of agents, captopril, was studied in the balloon injury/ polymer matrix/adventitial delivery model described above. Powdered captopril (Capoten$_f$, Squibb Pharmaceuticals) was embedded within EVAc matrices at 50% loading and delivered at a dosage of 10.79±0.1 mg, over the course of 14 days, to the adventitia of the carotid artery. The percent of luminal occlusion was 37.7±3.0.

EXAMPLE 5

Angiotensin II (AII) has been demonstrated to have both inhibitory and stimulatory effects on SMCs in tissue culture and has also been demonstrated to induce blood vessel growth in avascular structures such as the the rabbit cornea, independent of its hemodynamic effects. Matrices of ethylene-vinyl acetate copolymer were embedded with AII and sustained first order release demonstrated for more than one month. As the drug is potent in ng quantities, the EVAc matrix drug embedding technique was modified to include bovine serum albumin (BSA) as a carrier compound. When dry powdered AII was mixed with dry powdered BSA in a 1 to 500 ratio and then embedded within a EVAc matrix, the rate of BSA release dictated the rate of AII release. When this system was then placed in the balloon injury model described above, the vascular occlusion was noted and the number of blood vessels surrounding the implant counted and compared to control.

DOSE: 17 µg over the course of 14 days
LUMINAL OCCLUSION: 22.5–64%
INHIBITION COMPARED TO CONTROL: 0–62.6%
NUMBER OF VESSELS SURROUNDING AII IMPLANT: 27
NUMBER OF VESSELS SURROUNDING CONTROL IMPLANT: 6

Angiotensin II was able to induce a marked vascular response regardless of its ability to control SMC proliferation.

EXAMPLE 6

Heparin binding growth factors such as fibroblast growth factor (FGF) in culture are mitogens for a number of cell types and a potent angiogenesis factor in vivo that has no apparent effect on blood pressure. As growth factor activity may be lost if the factor is embedded in standard controlled release devices, an alternative method was used, taking of advantage the inherent ability of such growth factors to adhere to heparin.

FGF (Takeda Industries, Japan) was bound to heparin sepharose beads to stabilize the factor and to provide a solid carrier for minute quantities of the liquid growth factor. Aliquots of FGF were mixed with 2 ml of $I^{125}$FGF (1.2 mg/ml) and then incubated for 1 hour with the heparin sepharose beads. Subsequent release of FGF from the beads was followed in 0.15M NaCl buffer. Microspheres containing FGF were constructed by dropping a mixture of sodium alginate (1%) with heparin sepharose bead-bound FGF through a glass Pasteur pipette into a hardening solution of calcium chloride (1.5 weight %). Release kinetics were determined for microcapsules containing 6 ml of FGF and 2 ml of $I^{125}$FGF bound to 125 mg of the heparin sepharose beads in 500 ml of 0.15M NaCl. Heparin sepharose bead-laden FGF was incorporated within alginate microcapsules with 74% efficiency, and release of the FGF over time was retarded and prolonged in comparison to release from the unencapsulated beads. Bioactivity was retained by 87.6±12% of the factor preparation. Microspheres prepared as above were placed adjacent to noninjured and balloon endothelialized carotid arteries. In both blood vessels a significant increase in local vascularity was noted.

In addition to the examples described above, the method can be used in a laboratory setting to test the luminal repair-enhancing effect of a variety of potentially potent cell or tissue growth modulators previously discarded as ineffective because they do not act systemically, do not act in a similar fashion over a range of dosages, are degraded before they achieve their effects if applied systemically, or have side effects when delivered systemically.

A BRIEF DESCRIPTION OF THE DRAWING

Figure 1B:
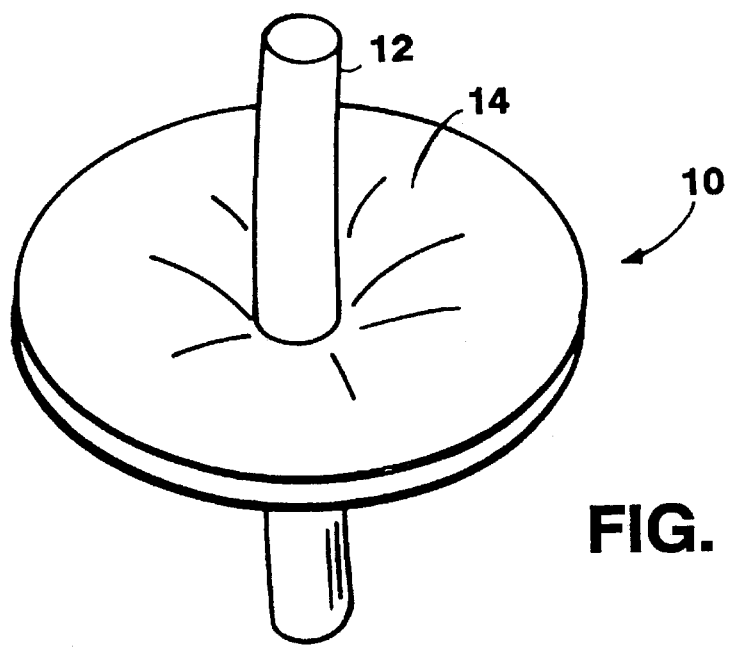

FIG. 1 is a highly diagrammatic representation of a torroidal structure (FIG. 1A) and (FIG. 1B) a disc according to the invention comprising a diffusion-controlled-release polymer body containing a drug. The polymer body 10 contains a centrally located hole through which suture 12 is threaded. The polymer body 10 has an outer coating 14 (e.g. if the polymer is a drug-loaded EVA matrix as described in U.S. Pat. No. 4,391,797, unloaded polymer can be used for the coating.

Other embodiments are within the following claims.

We claim:

1. A method of regulating repair of a wall of luminal tissue following injury at a location on said wall, said luminal tissue being vas deferens or fallopian tube, said method comprising, administering outside said luminal tissue at said location, a biocompatible polymer based compound-releasing system, said biocompatible polymer based compound-releasing system releasing heparin, said administering taking place over a period of at least 24 hours and being characterized by a rate and dosage that is less than 100 mg/day and is selected to be:

a) high enough to control proliferation of smooth muscle cells in said wall at said location; and b) low enough to avoid systemic heparin levels equivalent to an anticoagulant heparin level that would have a discernable effect on clotting function as measured by activated prothrombin tame (aPTT).

2. The method of claim 1 wherein said compound is non-anticoagulant heparin.

3. The method of claim 1 wherein said compound is anticoagulant heparin.

4. The method of claim 1 wherein said biocompatible polymer-based heparin releasing system comprises an aqueous gel or foam.

5. The method of claim 1 wherein said injury is surgical repair of said lumen at said location.

* * * * *

UNITED STATES PATENT AND TRADEMARK OFFICE
CERTIFICATE OF CORRECTION

PATENT NO. : 5,540,928
DATED : JULY 30, 1996
INVENTOR(S) : ELAZER R. EDELMAN ET AL.

It is certified that error appears in the above-identified patent and that said Letters Patent is hereby corrected as shown below:

Col. 1, line 5, insert --This invention was made with government support under grant HL17747 by the NIH. The government has certain rights in this invention--.

Title page, under section "U.S. PATENT DOCUMENTS" the reference listed as "Urquhart" should be --Urguhart--.

In col. 5, line 9, please delete "-20° C." and insert --20 °C--.

In col. 6, line 52, please delete "(5) 45.0±2.0" and insert --(5) 45.0+2.0--.

In col. 7, line 58, please delete "64%" and insert --54%--.

Signed and Sealed this

Twenty-sixth Day of September, 2000

Attest:

Q. TODD DICKINSON

*Attesting Officer*  *Director of Patents and Trademarks*